United States Patent [19]

Abou-Gharbia et al.

[11] Patent Number: 4,732,984
[45] Date of Patent: Mar. 22, 1988

[54] PIPERAZINOISOTHIAZOLONES WITH PSYCHOTROPIC ACTIVITY

[75] Inventors: Magid A. Abou-Gharbia, Wilmington, Del.; Guy A. Schiehser, Malvern; Scott J. Childress, Philadelphia, both of Pa.

[73] Assignee: American Home Products Corporation, New York, N.Y.

[21] Appl. No.: 893,507

[22] Filed: Aug. 5, 1986

Related U.S. Application Data

[63] Continuation-in-part of Ser. No. 788,315, Oct. 17, 1985, abandoned.

[51] Int. Cl.⁴ ............................................. C07D 417/14
[52] U.S. Cl. ..................................... 544/295; 544/238; 544/324; 544/331; 544/332; 544/357; 544/364; 544/367; 544/368; 540/575; 546/270; 548/149; 548/150; 548/151; 548/166
[58] Field of Search ............... 544/295, 238, 357, 364, 544/367, 368, 324, 331, 332; 540/575; 546/270; 548/149, 150, 151, 166

[56] References Cited

U.S. PATENT DOCUMENTS 3,227,715 1/1966 Bud ..................... 544/368
4,110,449 8/1978 Wade et al. ................... 544/368
4,113,728 9/1978 Baggaley .................. 544/368

FOREIGN PATENT DOCUMENTS 0109562 5/1984 European Pat. Off. .

OTHER PUBLICATIONS

Traber, et al., "Chemical Abstracts", vol. 101, 1984, Col. 101:204160r.
Dumpert, et al., "Chemical Abstracts", vol. 102, 1985, Col. 102:197866x, Col. 102:220896m.

Primary Examiner—Glennon H. Hollrah
Assistant Examiner—James H. Turnipseed
Attorney, Agent, or Firm—George Tarnowski

[57] ABSTRACT

There are disclosed compounds of the formula

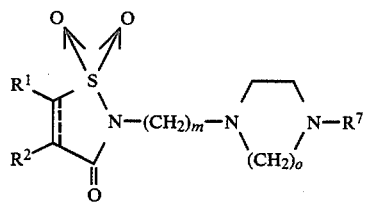

wherein
$R^1$ and $R^2$ are each, independently, hydrogen, lower alkyl, aryl or halo, or $R^1$ and $R^2$ taken together represent $-CH_2-$, $-CH_2CH_2-$, $-O-$, $-NH-$,

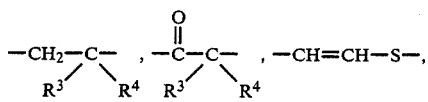

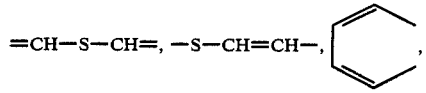

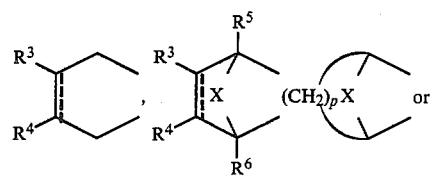

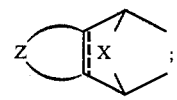

where the dotted lines represent optional double bonds;
$R^3$, $R^4$, $R^5$ and $R^6$ are each, independently, hydrogen, lower alkyl, aryl or halo;
$R^7$ is 2-pyridinyl, 2-pyrimidinyl, 2-pyrazinyl, 3-pyridazinyl or phenyl or any of the foregoing $R^7$ moieties substituted by lower alkyl, trifluoromethyl, cyano, nitro or halo, with the proviso that when $R^1$ and $R^2$ taken together represent

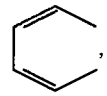

then $R^7$ is other than 2-pyridinyl, 2-pyrimidinyl or substituted pyrimidin-2-yl;
Z is $-(CH_2)_n-$, vinylene, $-O-$, or

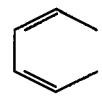

X is lower alkylene, vinylene, O or NH;
m is 2-5;
n is 0-4;
o is 1-3;
p is 1-4;
and the pharmaceutically acceptable salts thereof, and their use as antipsychotic/anxiolytic agents having a low liability for extrapyramidal side effects.

22 Claims, No Drawings

PIPERAZINOISOTHIAZOLONES WITH PSYCHOTROPIC ACTIVITY

This application is a continuation-in-part of U.S. Ser. No. 788,315, filed Oct. 17, 1985, now abandoned.

This invention relates to novel compounds having antipsychotic activity and being characterized by the general formula

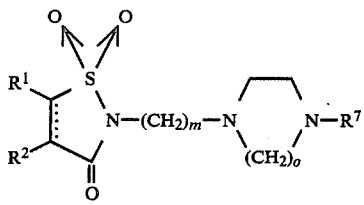

wherein
$R^1$ and $R^2$ are each, independently, hydrogen, lower alkyl, aryl or halo, or $R^1$ and $R^2$ taken together represent —CH₂—, —CH₂CH₂—, —O—, —NH—,

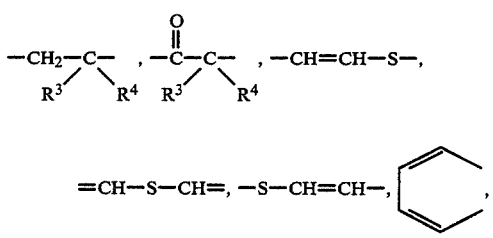

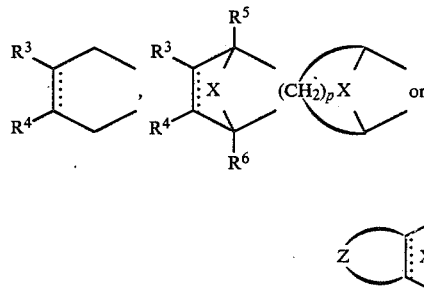

where the dotted lines represent optional double bonds;
$R^3$, $R^4$, $R^5$ and $R^6$ are each, independently, hydrogen, lower alkyl, aryl or halo;
$R^7$ is 2-pyridinyl, 2-pyrimidinyl, 2-pyrazinyl, 3-pyridazinyl or phenyl or any of the foregoing $R^7$ moieties substituted by lower alkyl, trifluoromethyl, cyano, nitro or halo, with the proviso that when $R^1$ and $R^2$ taken together represent

then $R^7$ is other than 2-pyridinyl, 2-pyrimidinyl or substituted pyrimidin-2-yl;
Z is —(CH₂)ₙ—, vinylene, —O—, or

X is lower alkylene, vinylene, O or NH;
m is 2-5;
n is 0-4;
o is 1-3;
p is 1-4;
and the pharmaceutically acceptable salts thereof.

The term "lower alkyl" refers to moieties having 1-6 carbon atoms in the carbon chain. The term "lower alkylene" refers to moieties having 1-4 carbon atoms in the carbon chain. The term "aryl" refers to moieties having 6-12 carbon atoms. The term "halo" refers to fluoro, chloro and bromo.

The compounds of the invention can form pharmacologically acceptable salts from pharmacologically acceptable organic and inorganic acids such as hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. For example, 3-isothiazolone 1,1-dioxide can be reacted with an appropriate diene to yield a precursor which when reacted with asuitable dihalo lower alkane affords an intermediate product:

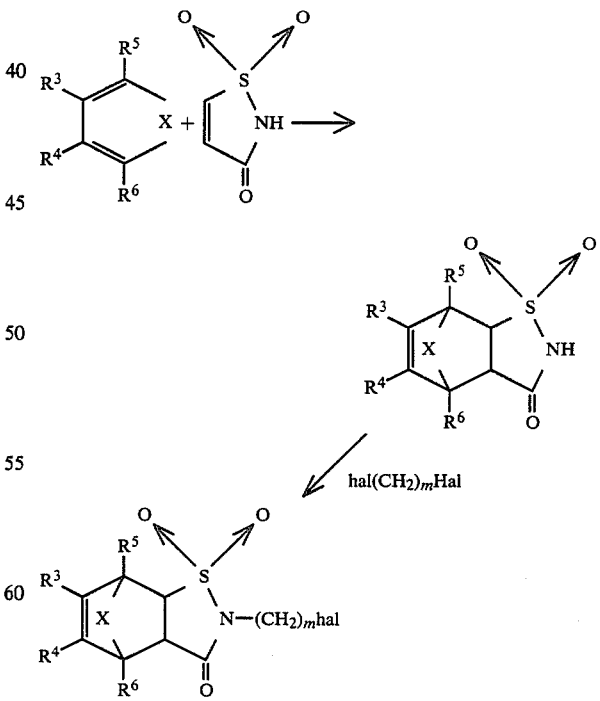

This intermediate product can then be reacted with an appropriately substituted 4-piperazine to yield the desired final product:

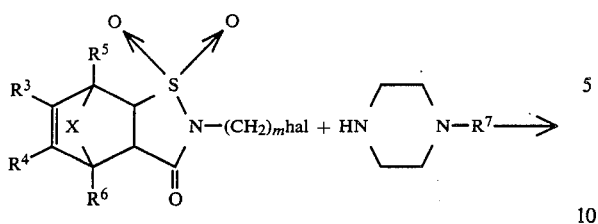

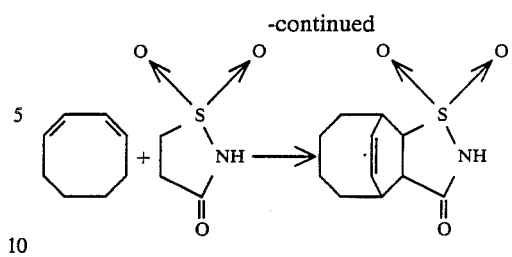

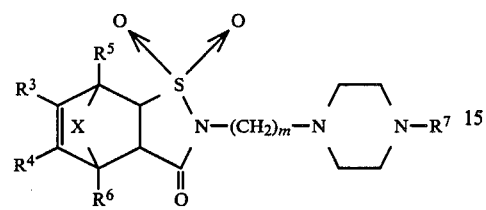

In the above sequences, $R^3$, $R^4$, $R^5$, $R^6$, $R^7$, X and m are as defined hereinbefore and hal is a halo atom, such as chloro or bromo. Compounds in which $R^1$ and $R^2$ taken together represent —CH=CH—S—, =CH—S—CH=, —S—CH=CH— or

can be prepared in like manner using an appropriate benzoisothiazolone 1,1-dioxide or thienoisothiazolone 1,1-dioxide as the starting material.

Compounds of the invention in which $R^1$ and $R^2$ taken together represent the moiety

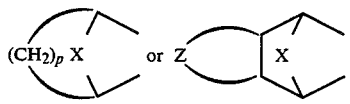

are prepared via the Diels-Alder addition outlined above, using a diene of appropriate ring size and degree of unsaturation. The following examples are illustrative:

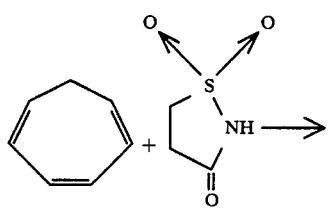

If instead of a Diels-Alder addition, the 3-isothiazolone 1,1-dioxide is subjected to epoxidation of carbene insertion, the corresponding final products can be obtained:

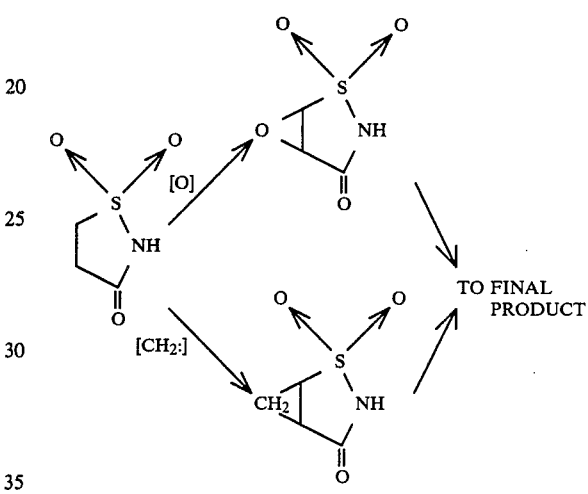

In an alternative preparative sequence, the 3-isothiazolone 1,1-dioxide can first be reacted with a dihalo lower alkane followed by reaction with an appropriately substituted 4-piperazine to yield the following intermediate:

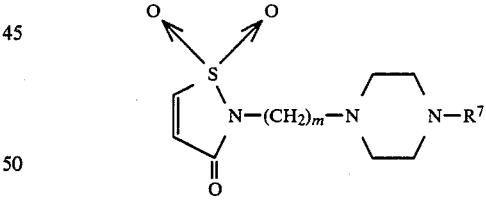

which can then be further reacted with appropriate reactants to yield desired final products. Thus, Diels-Alder addition of a diene, epoxidation or carbene insertion will yield the appropriate final product.

Compounds of the invention having the formula

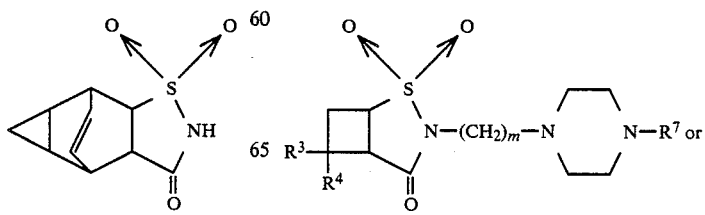

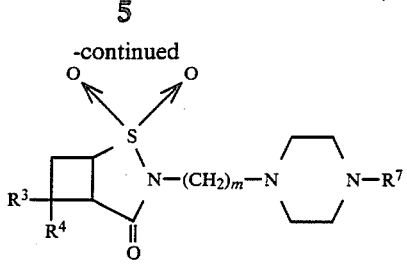

wherein R³ and R⁴ are as defined hereinbefore can be prepared by the same sequences as have been outlined, reacting a suitable ketene with the 3-isothiazolone 1,1-dioxide to obtain the desired intermediate, e.g.:

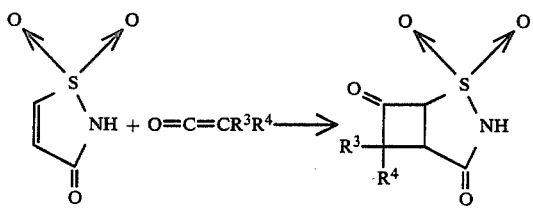

wherein R³ and R⁴ are as defined hereinbefore.

The saturated analogs of the compounds discussed above can be prepared by hydrogenating the intermediates or the final products using hydrogen and Pd/C as a catalyst.

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro[4.5]decane-7, 9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses, the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar lactose, pectin, dextrin, starch, gelatin, tragacanth, methylcellulose, sodium carboxymethylcellulose, low melting wax, cocoa butter and the like. Diluents, flavoring agents solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

3a,4,7,7a-Tetrahydro-2-[4-[4-(2-pyrimidinyl)-1-piperazinyl]butyl]-4,7-methano-1,2-benzisothiazol-3(2H)-one 1,1-dioxide, dihydrochloride, hemihydrate To a solution of 3 g (0.02 mol) of 3a,4,7,7a-tetrahydro-4,7-methano-1,2-benzisothiazol-3(2H)-one 1,1-dioxide in 50 mL of dimethylformamide is added 0.6 g (0.03 mol) of sodium hydride and the reaction mixture is stirred for 1 hour. While stirring, 3 g (0.02 mol) of 1-bromo-4-chlorobutane is added and stirring is continued for 48 hours. The dimethylformamide is removed under reduced pressure and the remaining semisolid is extracted with methylene chloride (3×100 mL), the methylene chloride layer is washed with water, dried (over anhydrous $Na_2SO_4$) and evaporated under reduced pressure. The semisolid which separates (4.0 g; 54% yield) is analyzed by IR and NMR, and spectral data are consistent for 3a,4,7,7a-tetrahydro-2-[4-chloro-1-butyl]-4,7-methano-1,2-benzisothiazol-3(2H)-one 1,1-dioxide. The title compound is prepared by dissolving 4 g (0.01 mol) of 3a,4,7,7a-tetrahydro-2-[4-chloro-1-butyl]-4,7-methano-1,2-benzisothiazol-3(2H)-one 1,1-dioxide in dimethylformamide (60 mL), to which is added 6 mL of triethylamine and 2.3 g (0.01 mol) of 4-(2-pyrimidinyl)piperazine. The reaction mixture is stirred for 48 hours at room temperature. The dimethylformamide is removed under reduced pressure and the remaining solid is dissolved in 30 mL of water and extracted with methylene chloride (3×300 mL). The methylene chloride extract is washed with water and dried (over anhydrous $Na_2SO_4$). Evaporation of the methylene chloride under reduced pressure gives a yellow semisolid. TLC analysis indicates the presence of the title compound and other impurities. The title compound is separated by HPLC on a silica gel column using 30% methanol-ethyl acetate as eluent. Evaporation of the solvent from the desired fraction $R_f$ 0.5 affords 0.8 g (20% yield) of the title compound, mp 118°–120° C., which is converted to the dihydrochloride by dissolving the free base in ethanol and adding ether saturated with hydrogen chloride, mp 220°–222° C.

Analysis for: $C_{20}H_{27}NSO_3.2HCl.\frac{1}{2}H_2O$. Calculated: C, 48.09; H, 6.01; N, 14.02; Cl, 14.66. Found: C, 48.27; H, 5.91; N, 14.01; Cl, 14.48.

EXAMPLE 2

3a,3,7,7a-Tetrahydro-2-[4-[4-(2-pyrimidinyl)-1-piperazinyl]butyl]-4,7-ethano-1,2-benzisothiazol-3(2H)-one 1,1-dioxide, dihydrochloride, hydrate The title compound is prepared following the procedure of Example 1 using 3a,4,7,7a-tetrahydro-4,7-ethano-1,2-benzisothiazol-3(2H)-one 1,1-dioxide instead of 3a,4,7,7a-tetrahydro-4,7-methano-1,2-benzisothiazol-3(2H)-one 1,1-dioxide and is converted to the dihydrochloride hydrate; mp 258°–260° C.

Analysis for: $C_{21}H_{29}N_5O_3S.2HCl.H_2O$. Calculated: C, 48.27; H, 6.37; N, 13.41. Found: C, 48.45; H, 6.38; N, 12.75.

EXAMPLE 3

3a,4,7,7a-Tetrahydro-5,6-dimethyl-2-[4-[4-(2-pyrimidinyl)-1-piperazinyl]butyl]-1,2-benzisothiazol-3(2H)-one 1,1-dioxide dihydrochloride The title compound is prepared using the procedure of Example 1 using 3a,4,7,7a-tetrahydro-5,6-dimethyl-1,2benzisothiazol-3(2H)-one 1,1-dioxide instead of 3a,4,7,7a-tetrahydro-4,7-methano-1,2-benzisothiazol-3(2H)-one 1,1-dioxide and is converted to the dihydrochloride salt, mp 160°–162° C.

Analysis for: $C_{21}H_{31}N_5SO_3.2HCl.1\frac{1}{2}H_2O$. Calculated: C, 47.27; H, 6.79; N, 13.12. Found: C, 47.13; H, 6.23; N, 12.85.

EXAMPLE 4

2-[4-[4-(6-chloro-2-pyrazinyl)-1-piperazinyl]butyl]-3a,4,7,7a-tetrahydro-5,6-dimethyl-1,2-benzisothiazol-3(2H)-one 1,1-dioxide, dihydrochloride The title compound is prepared using the procedure of Example 1 using 3a,4,7,7a-tetrahydro-5,6-dimethyl-1,2-benzisothiazol-3-(2H)-one 1,1-dioxide instead of 3a,4,7,7a-tetrahydro-4,7-methano-1,2-benzisothiazol-3(2H)-one 1,1-dioxide and 1-(6-chloro-2-pyrazinyl)piperazine instead of 4-(2-pyrimidinyl)piperazine. The final product is converted to its dihydrochloride salt, mp 158°–160° C.

Analysis for: $C_{21}H_{30}N_5ClSO_3.2HCl$. Calculated: C, 46.62; H, 5.96; N, 12.95. Found: C, 46.14; H, 5.43; N, 14.83.

EXAMPLE 5

2-[4-[4-(6-chloro-2-pyrazinyl)-1-piperazinyl]butyl]-3a,4,7,7a-tetrahydro-4,7-ethano-1,2-benzisothiazol-3(2H)-one 1,1-dioxide, hydrochloride A. 3a,4,7,7a-Tetrahydro-2-[4-bromobutyl]-4,7-ethano-1,2-benzisothiazol-3(2H)-one 1,1-dioxide A solution of 456 mg (19 mmol) of sodium hydride (prepared from 760 mg of 60% sodium hydride in mineral oil by pentane wash) in 40 ml of dimethylformamide is treated portionwise with 4.05 g (19 mmol) of 3a,4,7,7a-tetrahydro-4,7-ethano-1,2-benzisothiazol-3(2H)-one-1,1-dioxide at 0° C. The resulting solution is added dropwise to a solution of 12.3 g (57 mmol) of 1,4-dibromobutane in 40 ml of dimethylformamide. The mixture is maintained with stirring at room temperature for 22.5 hours. The solvent is removed under high vacuum and the residue partitioned between methylene chloride and water. The combined methylene chloride extracts are washed with brine and dried over MgSO₄. Filtration and removal of solvent in vacuo gives an oily solid which is triturated with ethyl ether and filtered to give 1.05 g of the title compound, mp 118°–122° C.

Analysis for: $C_{13}H_{18}BrNO_3S$. Calculated: C, 44.83; H, 5.21; N, 4.02. Found: C, 44.87; H, 5.07; N, 3.93.

B. 2-[4-[4-(6-chloro-2-pyrazinyl)-1-piperazinyl]butyl]-3a,4,7,7a-tetrahydro-4,7-ethano-1,2-benzisothiazol-3(2H)-one 1,1-dioxide,hydrochloride A solution of 1.0 g (2.9 mmol) of 3a,4,7,7a-tetrahydro-2-(4-bromobutyl)-4,7-ethano-1,2-benzisothiazol-3(2H)-one 1,1-dioxide in 25 ml of anhydrous dimethylformamide is treated with 1.6 g (16 mmol) of triethylamine and 866 mg (3.2 mmol) of 1-(6-chloro-2-pyrazinyl)-piperazine, monohydrochloride salt. The mixture is maintained at room temperature with stirring for 15 hours and then is partitioned between water and methylene chloride. The methylene chloride extracts are combined, dried over MgSO₄, filtered and rotoevaporated to give crude free base. Preparative HPLC (silica gel; ethyl acetate: methylene chloride (9:1)) followed by evaporation of the appropriate fractions, treatment with ethanolic hydrochloric acid and recrystallization from methanol gives the title compound: mp. 263°–267° C.

Analysis for: $C_{21}H_{28}N_5O_3SCl.HCl$. Calculated: C, 50.19; H, 5.82; N, 13.94. Found: C, 49.99; H, 5.78; N, 13.80.

EXAMPLE 6

4,4a,5,5a,6,6a-hexahydro-2-[4-[4-(2-pyrimidinyl)-1-piperazinyl]butyl]-4,6-etheno-2H-cyclopropa[f][1,2-]benzisothiazol-3(3aH)-one 1,1-dioxide,dihydrochloride A. 4,4a,5,5a,6,6a-hexahydro-2-(4-bromobutyl)-4,6-etheno-2H-cyclopropa[f][1,2]benzisothiazol-3(3aH)-one 1,1-dioxide A solution of 648 mg (27 mmol) of sodium hydride (prepared from 1.08 g of 60% sodium hydride in mineral oil by pentane wash) in 50 ml of dimethylformamide is treated portionwise at 10° C. with 5.45 g (24 mmol) of 4,4a,5,5a,6,6a-hexahydro-4,6-etheno-2H-cyclopropa[f][1,2]benzisothiazol-3(3aH)-one 1,1-dioxide. When gas evolution ceases, the solution is added dropwise to a solution of 25.9 g (120 mmol) of 1,4-dibromobutane in 100 ml of dimethylformamide. The mixture is maintained with stirring for 18 hours and then is partitioned between methylene chloride and aqueous sodium bicarbonate. The combined organic extracts are dried over MgSO₄, filtered, rotoevaporated and residual solvent removed under high vacuum. The solid residue is crystallized from isopropyl ether to give 4.5 g of the title compound: mp 96°–100° C.

Analysis for: $C_{14}H_{18}BrNO_3S$. Calculated: C, 46.67; H, 5.03; N, 3.88. Found: C, 45.28; H, 4.99; N, 4.42.

B. 4,4a,5,5a,6,6a-hexahydro-2-[4-[4-(2-pyrimidinyl)-1-piperazinyl]butyl]-4,6-etheno-2H-cyclopropa[f][1,2-]benzisothiazol-3(3aH)-one 1,1-dioxide, dihydrochloride A solution of 1.8 g (5 mmol) of 4,4a,5,5a,6,6a-hexahydro-2-(4-bromobutyl)-4,6-etheno-2H-cyclopropa[f][1,2-]benzisothiazol-3(3aH)-one 1,1-dioxide in 10 ml of dimethylformamide is added dropwise to a solution of 980 mg (6 mmol) of 4-(2-pyrimidinyl)piperazine dihydrochloride containing 3.0 g (30 mmol) of triethylamine and 1.6 g (5 mmol) of cesium carbonate over 2.5 hours. The mixture is stirred at room temperature for 17 hours and then is partitioned between methylene chloride and water. The combined organic extracts are dried over $MgSO_4$, filtered and evaporated under high vacuum to give crude product. Column chromatography (silica gel; ethyl acetate) gives 577 mg of free base. Treatment with ethanolic hydrochloric acid and recrystallization from absolute ethanol gives the title compound; mp. 233°–240° C.

Analysis for: $C_{22}H_{29}N_5O_3S.2HCl$. Calculated: C, 51.16; H, 6.05; N, 13.56. Found: C, 50.51; H, 5.97; N, 13.36.

EXAMPLE 7

2-[4-[4-(6-chloro-2-pyrzinyl)-1-piperazinyl]butyl]-4,4a,5,5a,6,6a-hexahydro-4,6-etheno-2H-cyclopropa[f][1,2]-benzisothiazol-3(3aH)-one 1,1-dioxide, hydrochloride The title compound is prepared following the procedure of Example 6B using 1-(6-chloro-2-pyrazinyl)piperazine hydrochloride instead of 4-(2-pyrimidinyl)piperazine dihydrochloride: mp. 255°–257° C. (dec).

Analysis for: $C_{22}H_{28}ClN_5O_3S.HCl$. Calculated: C, 51.56; H, 5.68; N, 13.61. Found: C, 51.76; H, 5.79; N, 13.51.

EXAMPLE 8

3aα,4β,7β,7aα-hexahydro-2-[4-[4-(6-chloro-2-pyrazinyl)-1-piperazinyl]butyl]-4,7-epoxy-1,2-benzisothiazol-3(2H)-one 1,1-dioxide, hydrochloride A solution of 3.5 g (10.4 mmol) of (3aα,4β,7β,7aα)-hexahydro-2-(4-bromobutyl)-4,7-epoxy-1,2-benzisothiazol-3(2H)-one 1,1-dioxide in 150 ml of dimethylformamide is treated with 8.6 g (84 mmol) of triethylamine and 4.9 g (21 mmol) of 1-(6-chloro-2-pyrazinyl)piperazine. The mixture is stirred at room temperature for 24 hours, 8.6 g (84 mmol) of triethylamine is added and stirring continued for 18 hours. The mixture is partitioned between methylene chloride and water. The combined organic extracts are dried over $MgSO_4$, filtered and evaporated to given an oil. Trituration with ethyl acetate gives a solid which is subjected to preparative HPLC (silica gel; ethyl acetate). The fractions containing the component at $R_f$ 0.15 (ethyl acetate) are evaporated and crystallized from ethyl acetate to give 1.1 g of free base of the title compound: mp 147°–149° C.

Analysis for: $C_{22}H_{28}ClN_5O_3S$. Calculated: C, 50.05; H, 5.75; N, 15.36. Found: C, 49.93; H, 5.74; N, 15.32.

The free base is treated with ethanolic hydrochloric acid and crystallized twice from absolute ethanol to give the title compound: mp 231°–235° C.

Analysis for: $C_{22}H_{28}ClN_5O_3S.HCl$. Calculated: C, 46.34; H, 5.33; N, 14.22. Found: C, 46.14; H, 5.39; N, 13.88.

EXAMPLE 9

2-[4-[4-(6-Chloro-2-pyrazinyl)-1-piperazinyl]butyl]-1,2-benzisothiazol-3(2H)-one 1,1-dioxide, hydrochloride A mixture of saccharin (3.69, 0.02 mol), sodium hydride 0.5 g, 1-bromo-4-chlorobutane (5.2 g, 0.03 mol) and 50 ml of dimethylformamide is stirred at room temperature for 48 hours.

The solvent is evaporated under reduced pressure and the brown residue is extracted with methylene chloride (3×200 ml). The methylene chloride extracts are collected, washed with water and dried (anhydrous $Na_2SO_4$). Evaporation of the methylene chloride under reduced pressure affords 5 g of 2-(4-chlorobutyl)-1,2-benzisothiazol-3(2H)-one 1,1-dioxide.

The title compound is prepared by dissolving 2.5 g (0.008 mol) of 2-(4-chlorobutyl)-1,2-benzisothiazol-3(2H)-one 1,1-dioxide in 50 ml of dimethylformamide and to that solution 2.5 g (0.01 mol) of 1-(6-chloro-2-pyrazinyl)piperazine hydrochloride and 5 ml of triethylamine are added. Stirring is continued for 48 hours. The solvent is removed under reduced pressure and the residue is partitioned between water and methylene chloride. The methylene chloride extracts are combined, dried over anhydrous $Na_2SO_4$, filtered and evaporated under reduced pressure to give crude base. Preparative HPLC (silica gel; ethylacetate:methylene chloride (9.1)) gives, following evaporation of the appropriate fractions ($R_f$ 0.5), the title compound, which is converted to the hydrochloride salt; mp 246°–249° C.

Analysis for: $C_{19}H_{22}ClN_5O_3.HCl$. Calculated: C, 48.30; H, 4.87; N, 14.83. Found: C, 48.03; H, 4.89; N, 14.06.

EXAMPLE 10

2-[4-[4-(6-Chloro-2-pyrazinyl)-1-piperazinyl]butyl]-thieno[3,4-d]-isothiazol-3(2H)-one 1,1-dioxide hydrochloride The title compound is prepared following the procedure of Example 9 using thiophene saccharin instead of saccharin and is converted to the hydrochloride salt; mp 255°–256° C.

Analysis for: $C_{17}H_{20}ClN_5S_2O_3.HCl$. Calculated: C, 42.67; H, 4.39; N, 14.64. Found: C, 43.09; H, 4.29; N, 14.84.

EXAMPLE 11

2-[4-[4-(3-Chloro-2-pyrazinyl)-piperazinyl]butyl]-1,2-benzisothiazol-3(2H)-one 1,1-dioxide, hydrochloride The title compound is prepared following the procedure of Example 9 using 1-(3-chloro-2-pyrazinyl)piperazine hydrochloride instead of 1-(6-chloro-2-pyrazinyl)-piperazine hydrochloride and is converted to the hydrochloride salt; mp 229°–231° C.

Analysis for: $C_{19}H_{22}ClN_5O_3SHCl.\frac{1}{2}H_2O$. Calculated: C, 47.40; H, 4.98; N, 14.55. Found: C, 47.61; H, 4.94; N, 14.49.

EXAMPLE 12

2-[4-[4-(3-Chloro-2-pyrazinyl)-1-piperazinyl]butyl]-thieno[3,4-d]isothiazol-3(2H)-one 1,1-dioxide, hydrochloride, hemipentahydrate The title compound is prepared following the procedure of Example 9 using thiophene saccharin instead of saccharin and 1-(3-chloro-2-pyrazinyl)piperazine hydrochloride instead of 1-(6-chloro-2-pyrazinyl)piperazine hydrochloride and is converted to the hydrochloride salt; mp 243°–245° C.

Analysis for: $C_{17}H_{20}N_5S_2ClO_3 \cdot HCl \cdot 2\frac{1}{2}H_2O$. Calculated: C, 38.90; H, 4.77; N, 13.37. Found: C, 38.20; H, 4.93; N, 13.85.

EXAMPLE 13

2-[4-[4-(3-Chloro-2-pyrazinyl)-1-piperazinyl]butyl]-3a,4,7,7a-tetrahydro-5,6-dimethyl-1,2-benzisothiazol-3(2H)-one 1,1-dioxide, hydrochloride, hydrate The title compound is prepared using the procedure of Example 1, using 3a,4,7,7a-tetrahydro-5,6-dimethyl-1,2-benzisothiazol-3(2H)-one 1,1-dioxide instead of 3a,4,7,7a-tetrahydro-4,7-methano-1,2-benzisothiazol-3(2H)-one 1,1-dioxide and 1-(3-chloro-2-pyrazinyl)piperazine hydrochloride instead of 1-(2-pyrimidinyl)piperazine and is converted to the hydrochloride salt; mp 95°–97° C.

Analysis for: $C_{21}H_{30}ClN_5SO_3 \cdot HCl \cdot H_2O$. Calculated: C, 48.36; H, 6.14; N, 13.43. Found: C, 48.80; H, 6.25; N, 13.30.

EXAMPLE 14

2-[4-[4-(6-Chloro-2-pyrazinyl)-1-piperazinyl]butyl]-3a,4,7,7a-tetrahydro-4,7-methano-1,2-benzisothiazol-3(2H)-one 1,1-dioxide, dihydrochloride The title compound is prepared following the procedure of Example 1 and using 1-(6-chloro-2-pyrazinyl)piperazine hydrochloride instead of 1-(2-pyrimidinyl)piperazine and is converted to the hydrochloride salt; mp 235°–237° C.

Analysis for: $C_{20}H_{26}ClN_5SO_3 \cdot 2HCl$. Calculated: C, 45.75; H, 5.52; N, 13.34. Found: C, 46.06; H, 5.55; N, 12.97.

EXAMPLE 15

2-[4-[4-(2-Pyrimidinyl)-1-piperazinyl]butyl]-3a,4,5,6,7,7a-hexahydro-4,7-methano-1,2-benzisothiazol-3(2H)-one 1,1-dioxide, dihydrochloride, hemihydrate The title compound is prepared following procedure of Example 1 and using 3a,4,5,6,7,7a-hexahydro-4,7-methano-1,2-benzisothiazol-3(2H)-one 1,1-dioxide instead of 3a,4,7,7a-tetrahydro-4,7-methano-1,2-benzisothiazol-3(2H)-one 1,1-dioxide and is converted to the hydrochloride salt; mp 214°–215° C.

Analysis for: $C_{20}H_{29}SN_5O_3 \cdot 2HCl \cdot \frac{1}{2}H_2O$. Calculated: C, 47.90; H, 6.38; N, 13.97. Found: C, 48.04; H, 6.15; N, 13.74.

EXAMPLE 16

2-[4-[4-(6-Chloro-2-pyrazinyl)-1-piperazinyl]butyl]-3a,4,5,6,7,7a-hexahydro-4,7-methano-1,2-benzisothiazol-3(2H)-one 1,1-dioxide, hydrochloride The title compound is prepared following the procedure of Example 1 and using 3a,4,5,6,7,7a-hexahydro-4,7-methano-1,2-benzisothiazol-3(2H)-one, 1,1-dioxide instead of 3a,4,7,7a-tetrahydro-4,7-methano-1,2-benzisothiazol-3(2H)-one 1,1-dioxide and 1-(6-chloro-2-pyrazinyl)-1-piperazine hydrochloride instead of 1-(2-pyrimidinyl)piperazine and is converted to the hydrochloride salt; mp 240°–242° C.

Analysis for: $C_{20}H_{28}ClSN_5O_3 \cdot HCl$. Calculated: C, 48.97; H, 5.91; N, 14.28. Found: C, 49.15; H, 6.00; N, 14.08.

EXAMPLE 17

Hexahydro-2-[4-[4-(2-pyrimidinyl)-1-piperazinyl]butyl-4,6-ethano-2H-cycloprop[f]-1,2-benzisothiazol-3(2H)-one 1,1-dioxide, hydrochloride A. Hexahydro-4,6-ethano-2H-cycloprop[f]-1,2-benzisothiazol-3(3aH)-one 1,1-dioxide To a stirred suspension of 3-isothiazolone 1,1-dioxide in 100 ml of xylene, 5.2 ml (0.05 mol) of 1,3,5-cycloheptatriene is added. The reaction mixture is refluxed 5 hrs, then allowed to cool. The separated solid is filtered and dried to afford 2.2 g of 4,4a,5,5a,6,6a-hexahydro-4,6-ethano-2H-cycloprop[f]-1,2-benzisothiazol-3(2H)-one 1,1-dioxide; mp 179°–182° C.

A solution of 2.2 g of 4,4a,5,5a,6,6a-hexahydro-4,6-etheno-2H-cycloprop[f]-1,2-benzisothiazol-3(2H)-one 1,1-dioxide in 50 ml of ethanol is hydrogenated in the presence of 2 g of 10% Pd/C for 24 hours. The catalyst is filtered and the solvent is evaporated under reduced pressure to afford 2 g of hexahydro-4,6-ethano-2H-cycloprop-[f]1,2-benzisothiazol-3(3aH)-one 1,1-dioxide.

B. Hexahydro-2-[4-[4-(2-pyrimidinyl)-1-piperazinyl]butyl]-4,6-ethano-2H-cycloprop[f]-1,2-benzisothiazol-3(2H)-one 1,1-dioxide, hydrochloride The title compound is prepared following the procedure of Example 6 using hexahydro-4,6-ethano-2H-cycloprop[f]-1,2-benzisothiazol-3(3aH)-one 1,1-dioxide instead of 4,4a,5,5a,6,6a-hexahydro-4,6-etheno-2H-cycloprop[f]-1,2-benzisothiazol-3(3aH)-one 1,1-dioxide and is converted to the hydrochloride salt; mp 250°–251° C.

Analysis for: $C_{22}H_{31}N_5O_3S \cdot HCl$. Calculated: C, 54.81; H, 6.69; N, 14.53. Found: C, 54.61; H, 6.70; N, 14.02.

EXAMPLE 18

2-[4-[4-(6-Chloro-2-pyrazinyl)-1-piperazinyl]butyl]-4,4a,5,5a,6,6a-hexahydro-4,6-etheno-2H-cycloprop[f]-1,2-benzisothiazol-3(2H)-one 1,1-dioxide, hydrochloride The title compound is prepared following the procedure of Example 6 using 1-(6-chloro-2-pyrazinyl)-piperazine hydrochloride instead of 1-(2-pyrimidinyl)-piperazine and is converted to the hydrochloride salt; mp 255°–257° C.

Analysis for: $C_{22}H_{28}ClN_5O_3S \cdot HCl$. Calculated: C, 51.36; H, 5.68; N, 13.61. Found: C, 51.76; H, 5.79; N, 13.51.

EXAMPLE 19

(3a$\alpha$,4$\beta$,7$\beta$,7a$\alpha$)-Hexahydro-2-[4-[4-(2-pyrazinyl)-1-piperazinyl]butyl]-4,7-epoxy-1,2-benzisothiazol-3(2H)-one 1,1-dioxide, dihydrochloride, hemihydrate A. (3a$\alpha$,4$\beta$,7$\beta$,7a$\alpha$)Hexahydro-4,7-epoxy-1,2-benzisothiazol-3(2H)-one 1,1-dioxide A mixture of 5.2 g of 3-isothiazolone 1,1-dioxide and 5 ml of furan in 100 ml benzene is refluxed for 2 hours. An additional 5 ml of furan is added and the refluxing is continued for an additional hour; after cooling, the separated solid is filtered. It affords 7.5 g of a 2:1 mixture of exo:endo cycloadduct; mp 170°–171° C. The exoadduct is (3a$\alpha$,4$\beta$,7$\beta$,7a$\alpha$)-tetrahydro-4,7-epoxy-1,2-benzisothiazol-3(2H)-one 1,1-dioxide. The endoadduct is (3a$\alpha$,4$\alpha$,7$\alpha$,7a$\alpha$)-tetrahydro-4,7-epoxy-1,2-benzisothiazol-3(2H)-one 1,1-dioxide. The exo product (10.0 g) is dissolved in 100 ml of tetrahydrofuran and is hydrogenated over 2 g of Pd/C (10%) for 30 minutes. The catalyst is filtered and the solvent is evaporated under reduced pressure to afford 9.8 g of the reduced cycloadduct (3aα,4β,7β,7aα)-hexahydro-4,7-epoxy-1,2-benzisothiazol-3(2H)-one 1,1-dioxide; mp 209°–212° C.

Analysis for: $C_7H_9SNO_4$. Calculated: C, 41.85; H, 4.52; N, 6.89. Found: C, 41.37; H, 4.46; N, 6.89.

B. 3aα,4β,7β,7aα)-Hexahydro-2-[4-[4-(2-pyrazinyl)-1-piperazinyl]butyl]-4,7-epoxy-1,2-benzisothiazol-3(2H)-one 1,1-dioxide, dihydrochloride, hemihydrate The title compound is prepared following the procedure of Example 8, using 1-(2-pyrazinyl)piperazine hydrochloride instead of 1-(6-chloro-2-pyrazinyl)piperazine hydrochloride and is converted to the hydrochloride salt; mp 186°–198° C.

Analysis for: $C_{19}H_{27}N_5SO_4$. Calculated: C, 45.32; H, 6.01; N, 13.91. Found: C, 45.40; H, 5.91; N, 13.51.

EXAMPLE 20

(3aα,4α,7α,7aα)-2-[4-[4-(6-Chloro-2-pyrazinyl)-1-piperazinyl]butyl]hexahydro-4,7-epoxy-1,2-benzisothiazol-3(2H)-one 1,1-dioxide, hydrochloride The title compound is prepared following the procedure of Example 8, using (3aα,4α,7α,7aα)-hexahydro-4,7-epoxy-1,2-benzisothiazol-3(2H)-one 1,1-dioxide instead of (3a α,4β,7β,7aα)-hexahydro-4,7-epoxy-1,2-benzisothiazol-3(2H)-one 1,1-dioxide and is converted to the hydrochloride salt; mp 268°–277° C.

Analysis for: $C_{19}H_{26}ClN_5SO_4 \cdot HCl$. Calculated: C, 46.34; H, 5.53; N, 14.22. Found: C, 46.34; H, 5.48; N, 14.01.

EXAMPLE 21

3a,4,4a,6a,7,7a-Hexahydro-2-[4-[4-(2-pyrimidinyl)-1-piperazinyl]butyl]-4,7-ethenocyclobut[f]-1,2-benzisothiazol-3(2H)-one 1,1-dioxide, dihydrochloride A. 3a,4a,6a,7,7a-Hexahydro-4,7-ethenocyclobut[f]-1,2-benzisothiazol-3(2H)-one 1,1-dioxide To a boiling solution of 3-isothiazolone 1,1-dioxide (2.8 g) is added 2 g of cyclooctatetraene portionwise and refluxing is continued for 16 hrs. The mixture is decanted and chilled in ice. The resulting crystalline product is separated and filtered to afford 1.92 g of 3a,4a,6a,7,7a-hexahydro-4,7-ethenocyclobut[f]-1,2-benzisothiazol-3(2H)-one 1,1-dioxide; mp 207°–215° C.

Analysis for: $C_{11}H_{11}SNO_3$. Calculated: C, 53.76; H, 4.52; N, 5.89. Found: C, 53.68; H, 4.67; N, 5.90.

B. 3a,4,4a,6a,7,7a-Hexahydro-2-[4-[4-(2-pyrimidinyl-1-piperazinyl]butyl]-4,7-ethenocyclobut[f]-1,2-benzisothiazol-3(2H)-one 1,1-dioxide dihydrochloride The title compound is prepared following the procedure of Example 1, using 3a,4a,6a,7,7a-hexahydro-4,7-ethenocyclobut[f]-1,2-benzisothiazol-3(2H)-one 1,1-dioxide instead of 3a,4,7,7a-tetrahydro-4,7-methano-1,2-benzisothiazol-3(2H)-one 1,1-dioxide and is converted to the hydrochloride salt; mp 222°–234° C.

Analysis for: $C_{23}H_{29}N_5O_3S \cdot 2HCl$. Calculated: C, 52.27; H, 5.91; N, 13.25. Found: C, 52.82; H, 5.89; N, 12.65.

EXAMPLE 22

The compounds of the invention are tested in an assay to determine their ability to antagonize apomorphine-induced stereotyped behavior. The assay measures the in vivo dopamine receptor blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80 ® in water, are administered at several dose levels to male mice (6/dose level). A control group, run simultaneously with drug groups, receives equal volumes of solvent. Thirty minutes later (i.p. administration), drug-treated and control mice are challenged with 10 mg/kg apomorphine s.c. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| STANDARD COMPOUNDS: $ED_{50}$ and 95% confidence interval, mg/kg | |
|---|---|
| | intraperitoneal |
| Haloperidol | 1.37 (0.88–2.34) |
| Chloropromazine | 8.48 (4.79–16.38) |
| Clozapine | 30.06 (19.42–48.21) |

The compounds of the invention and buspirone, when tested in this assay are inactive, evidencing a low potential for exhibiting extrapyramidal side effects,such as pseudoparkinsonism, tardive dyskinesia and the like.

EXAMPLE 23

The compounds of the invention are further studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The assay is carried out as follows:

Several rats are decapitated and the brains are rapidly removed. Limbic brain tissue (nucleus accumbens, septal area, olfactory tubercle) is dissected and homogenized on ice in 9 volumes of buffer (50 mM Tris-HCl, 120 mM NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for three 15-sec bursts. The homogenate is then diluted 4-fold with buffer and centrifuged at 30,000×g for 20 min, and the supernatant is discarded. The pellet is resuspended in the same volume of buffer and recentrifuged as before, again discarding the supernatant. This pellet is then resuspended in the same volume of buffer used in the homogenization, and the protein content of this preparation is assyed by the Lowry method. The homogenate is stored frozen at −70° C. until use.

Thirty μL of the homogenate (0.02–0.3 mg protein/sample) are incubated with 0.3 nM $^3H$-spiroperidol (New England Nuclear) and various concentrations of test drug in a final volume of 1 ml of the above buffer for 10 min in a 37° C. water bath. At the end of the incubation, 3 ml of cold 50 mM Tris-HCl, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 min with 10 ml of Hydrofluor (National Diagnostics) scintillation cocktail. The vials are then counted in a Packard 460CD scintillation counter.

Specific binding is defined as total binding less binding in the presence of 1 μM (+)butaclamol. Binding in the presence of various concentrations of test drug is expressed as a per cent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H-\text{Spiroperidol}]}{K_D}}$$

where $K_D = 0.3$ nM for for spiroperidol binding.

| STANDARD COMPOUNDS | $K_i$ and 95% confidence interval |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention, and the prior art compound buspirone (8-[4-[4-(2-pyrimidinyl)-1-piperazinyl]butyl]-8-azaspirol[4.5]-decane-7,9-dione) in this assay are presented in Table 1.

TABLE 1

| Compound of Example No. | Limbic D-2 Binding ($K_i$ nM) |
|---|---|
| Buspirone | 119 |
| 1 | 1100 (no confidence interval) |
| 2 | 2000 (850–11,500) |
| 3 | 21% inhibition at 1 μM |
| 6 | 1407 |
| 8 | 36% inhibition at 10 μM |
| 11 | 493 |
| 13 | 507 |
| 18 | 1031 |

The results show that the compounds of the invention display a very weak effect, evidencing a low potential for extrapyramidal side effects.

EXAMPLE 24

The antipsychotic activity of the compounds of the invention is assessed via the conditioned avoidance (discrete trial) test. This test has excellent clinical correlation for antipsychotic activity.

The test is carried out as follows:

Male CD rats (Charles River) maintained at approximately 400–450 gm body weight are used. Rats trained previously are placed in plexiglass experimental chambers equipped with a response lever, house light, and sonalert. A steel grid floor is wired for presentation of electric shock. Each trial consists of a fifteen-second warning tone (conditioned stimulus), continuing for an additional fifteen seconds accompanied by electric shock, (unconditioned stimulus). The rat can terminate a trial at any point by depression of the response lever. A response during the initial fifteen-second warning tone ends the trial before shock delivery and is considered an avoidance response, while a response occurring during shock delivery is an escape response. Trials are presented on a variable interval schedule of two minutes. The session consists of sixty trials. Animals are run two to three times weekly with control sessions always preceding a drug run, and with at least one day intervening, compounds are administered i.p. or p.o. at appropriate pre-treatment times to a minimum of five to six rats at each dose level over a range of doses.

The following experimental parameters are recorded by computer: (1) the number of intertrial interval responses, (2) the number of avoidance responses, (3) the number of escape responses, and (4) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB)is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential antipsychotic compounds suppress avoidance responding and increase escape responding.

| Standard Compounds: | $AB_{50}$ (mg/kg i.p.) |
|---|---|
| Spiperone | 0.13 |
| Haloperidol | 0.18 |
| Chlorpromazine | 2.50 |
| Thioridazine | 8.61 |
| Clozapine | 10.82 |

The results for a compound of this invention in this test is presented in Table 2.

TABLE 2

| Compound of Example No. | $AB_{50}$ mg/kg | |
|---|---|---|
| 1 | 45.39 | perorally administered |
| 8 | 34.28 | perorally administered |
| 14 | 78.2 | perorally administered |
| 19 | 47.9 | perorally administered |
| 21 | 39.37 | perorally administered |
| Buspirone | 31.96 | perorally administered |

Compounds of Example numbers 15, 16, 17, 18, 20, and 21 all showed activity in this assay at 40 mg/kg perorally administered.

The results show the compounds tested to have activity comparable to that of buspirone when orally administered.

EXAMPLE 25

Another test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber ($10\frac{1}{2}''\times 6\frac{3}{4}''\times 11\frac{7}{8}''$ high) and an elevated chamber or shelf ($5\frac{7}{8}''\times 6\frac{7}{8}''\times 5\frac{3}{4}''$). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance responding and the dose calculated to produce a 50% block in avoidance responding ($AB_{50}$) is obtained from a dose-effect regression line fitted by the method of least squares. Potential antipsychotic compounds suppress avoidance responding and increase escape responding.

| Standard Compounds: | $AB_{50}$ (mg/kg i.p.) |
|---|---|
| Haloperidol | 0.19 |
| Chlorpromazine | 3.69 |
| Clozapine | 6.94 |
| Buspirone | 9.44 |

The results for compounds of this invention in this test are presented in Table 3.

TABLE 3

| Compound of Example No. | Active at mg/kg |
|---|---|
| 1 | 40 (i.p.)* |
| 2 | 40 (i.p.) |
| 3 | 40 (i.p.) |
| 5 | 40 (i.p.) |
| 6 | 20 (i.p.) |
| 8 | 40 (i.p.) |
| 9 | 40 (i.p.) |
| 11 | 40 (i.p.) |
| 12 | 40 (i.p.) |
| 13 | 40 (i.p.) |
| 14 | 40 (i.p.) |
| 15 | 40 (i.p.) |
| 16 | 40 (i.p.) |
| 17 | 40 (i.p.) |
| 18 | 40 (i.p.) |
| 19 | 40 (i.p.) |
| 20 | 40 (i.p.) |

TABLE 3-continued

| Compound of Example No. | Active at mg/kg |
|---|---|
| 21 | 40 (i.p.) |

*(i.p.) = intraperitoneally adminstered drug

The results show that compounds of the invention are active intraperitoneally in this test.

What is claimed is:

1. A compound having the formula

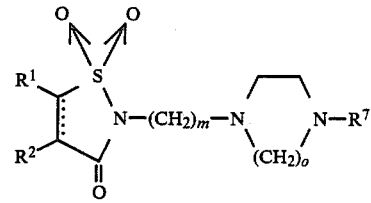

wherein
$R^1$ and $R^2$ are each, independently, hydrogen, lower alkyl, aryl of 6 to 12 carbon atoms or halo, or $R^1$ and $R^2$ taken together represent —CH=CH—S—, =CH—S—CH=, —S—CH=CH—,

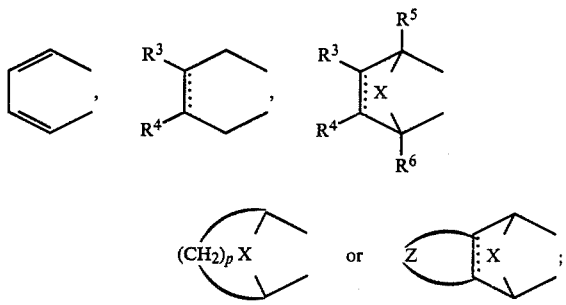

where the dotted lines represent optional double bonds;
$R^3$, $R^4$, $R^5$ and $R^6$ are each, independently, hydrogen, lower alkyl, aryl of 6 to 12 carbon atoms or halo;
$R^7$ is 2-pyridinyl, 2-pyrimidinyl, 2-pyrazinyl, 3-pyridazinyl or phenyl or any of
the foregoing $R^7$ moieties substituted by lower alkyl, trifluoromethyl,
cyano, nitro or halo, with the proviso that when $R^1$ and $R^2$ taken together represent

then $R^7$ is other than 2-pyridinyl, 2-pyrimidinyl, substituted pyrimidin-2-yl, phenyl or substituted phenyl;
Z is —$(CH_2)_n$— or vinylene;
X is lower alkylene, vinylene or O;
m is 2–5;
n is 1–4;
o is 1–3;
p is 1–4;
and the pharmaceutically acceptable salts thereof.

2. The compound of claim 1, having the name 3a,4,7,7a-tetrahydro-2-[4-[4-(2-pyrimidinyl)-1-piperazinyl]- butyl]-4,7-methano-1,2-benzisothiazol-3(2H)-one 1,1-dioxide.

3. The compound of claim 1, having the name 3a,3,7,7a-tetrahydro-2-[4-[4-(2-pyrimidinyl)-1-piperazinyl]butyl]-4,7-ethano-1,2-benzisothiazol-3(2H)-one 1,1-dioxide.

4. The compound of claim 1, having the name 3a,4,7,7a-tetrahydro-5,6-dimethyl-2-[4-[4-(2-pyrimidinyl)-1-piperazinyl]butyl]-1,2-benzisothiazol-3(2H)-one 1,1-dioxide.

5. The compound of claim 1, having the name 2-[4-[4-(6-chloro-2-pyrazinyl)-1-piperazinyl]butyl]-3a,4,7,7a-tetrahydro-5,6-dimethyl-1,2-benzisothiazol-3(2H)-one 1,1-dioxide.

6. The compound of claim 1, having the name 2-[4-[4-(6-chloro-2-pyrazinyl)-1-piperazinyl]butyl]-3a,4,7,7a-tetrahydro-4,7-ethano-1,2-benzisothiazol-3(2H)-one 1,1-dioxide.

7. The compound of claim 1, having the name 4,4a,5,5a,6,6a,-hexahydro-2-[4-[4-(2-pyrimidinyl)-1-piperazinyl]butyl]-4,6-etheno-2H-cyclopropa[f][1,2-]benzisothiazol-3(3aH)-one 1,1 -dixiode.

8. The compound of claim 1, having the name 2-[b 4-[4-(6-chloro-2-pyrazinyl)-1-piperazinyl]butyl]-4,4a,5,5a,6,6a-hexahydro-4,6-etheno-2H-cyclopropa[f][1,2]-benzisothiazol-3(3aH)-one 1,1-dioxide.

9. The compound of claim 1, having the name 3a-,α,4β,7β,7a α-hexahyro-2-[4-[4-(6-chloro-2-pyrazinyl)-1-piperazinyl]butyl]-4,7-epoxy-1,2-benzisothiazol-3(2H)-one 1,1-dioxide.

10. The compound of claim 1, having the name 2-[4-[4-(6-chloro-2-pyrazinyl)-1-piperazinyl]butyl]-1,2-benzisothiazol-3(2H)-one 1,1-dioxide.

11. The compound of claim 1, having the name 2-[4-[4-(6-chloro-2-pyrazinyl)-1-piperazinyl]butyl]-thieno[3,4-d]isothiazol-3(2H)-one 1,1-dioxide.

12. The compound of claim 1, having the name 2-[4-[4-(3-chloro-2-pyrazinyl)-piperazinyl]butyl]1,2-benzisothiazol-3(2H)-one 1,1-dixiode.

13. The compound of claim 1, having the name 2-[4-[4-(3-chloro-2-pyrazinyl)-1-piperazinyl]butyl]-thieno[3,4-d]isothiazol-3(2H)-one 1,1-dioxide.

14. The compound of claim 1, having the name 2-[4-[4-(3-chloro-2-pyrazinyl)-1-piperazinyl]butyl]-3a,4,7,7a-tetrahydro-5,6-dimethyl-1,2-benzisothiazol-3(2H)-one 1,1-dioxide.

15. The compound of claim 1, having the name 2-[4-[4-(6-chloro-2-pyrazinyl)-1-piperazinyl]butyl]-3a,4,7,7a-tetrahydro-4,7-methano-1,2-benzisothiazol-3(2H)-one 1,1-dioxide.

16. The compound of claim 1, having the name 2-[4-[4-(2-pyrimidinyl)-1-piperazinyl]butyl]-3a,4,5,6,7,7a-hexahydro-4,7-methano-1,2-benzisothiazol-3(2H)-one 1,1-dioxide.

17. The compound of claim 1, having the name 2-[4-[4-(6-chloro-2-pyrazinyl)-1-piperazinyl]butyl]-3a,4,5,6,7,7a-hexahydro-4,7-methano-1,2-benzisothiazol-3(2H)-one 1,1-dioxide.

18. The compound of claim 1, having the name hexahydro-2-[4-[4-(2-pyrimidinyl)-1-piperazinyl]butyl]-4,6-ethano-2H-cycloprop[f]-1,2-benzisothiazol-3(2H)-one 1,1-dioxide.

19. The compound of claim 1, having the name 2-[4-[4-(6-chloro-2-pyrazinyl)-1-piperazinyl]butyl]-4,4a,5,5a,6,6a-hexahydro-4,6-etheno-2H-cycloprop[f]-1,2-benzisothiazol-3(2H)-one 1,1-dioxide.

20. The compound of claim 1, having the name (3a α, 4β,7β,7a α)-hexahydro-2-[4-[4-(2-pyrazinyl)-1-piperazinyl]butyl]-4,7-epoxy-1,2-benzisothiazol-3(2H)-one 1,1-dioxide.

21. The compound of claim 1, having the name (3aα,-4α,7α,7aα)-2-[4-[4-(6-chloro-2-pyrazinyl)-1-piperazinyl]butyl]hexahydro-4,7-epoxy-1,2-benzisothiazol-3(2H)-one 1,1-dioxide.

22. The compound of claim 1, having the name 3a,4,4a,6a,7,7a-hexahydro-2-[4-[4-(2-pyrimidinyl)-1-piperazinyl]butyl]-4,7-ethenocyclobut[f]-1,2-benzisothiazol-3(2H)-one 1,1-dioxide.

* * * * *